(12) United States Patent
Burke et al.

(10) Patent No.: US 8,449,680 B2
(45) Date of Patent: May 28, 2013

(54) METHOD AND APPARATUS FOR TREATING A CELLULOSIC FEEDSTOCK (75) Inventors: Murray J. Burke, Oakville (CA); Sunalie N. Hillier, Georgetown (CA)

(73) Assignee: Mascoma Canada Inc., Georgetown, Ontario (CA)

( * ) Notice: Subject to any disclaimer, the term of this patent is extended or adjusted under 35 U.S.C. 154(b) by 529 days.

(21) Appl. No.: 12/181,666

(22) Filed: Jul. 29, 2008

(65) Prior Publication Data

US 2010/0024808 A1 Feb. 4, 2010

(30) Foreign Application Priority Data

Jul. 24, 2008 (CA) .................................. 2638152

(51) Int. Cl.
*C13K 1/02* (2006.01)

(52) U.S. Cl. ........... 127/37; 127/1; 536/124; 366/169.1; 366/170.3; 366/172.1; 366/297

(58) Field of Classification Search .................. 366/144, 366/147, 149, 151.1, 153.3, 167.1, 168.1, 366/172.1, 172.2, 173.1, 169.1, 170.3, 297; 127/1, 31; 536/124
See application file for complete search history.

(56) References Cited

U.S. PATENT DOCUMENTS

| 319,299 | A | 6/1885 | Morgan |
|---|---|---|---|
| 459,113 | A | 9/1891 | Rymal |
| 1,073,425 | A | 9/1913 | Lambert |
| 1,106,736 | A | 8/1914 | Schuller |
| 1,247,153 | A * | 11/1917 | Roberts .................. 366/104 |
| 1,560,855 | A | 11/1925 | Queneau |
| 2,080,327 | A | 5/1937 | McKinnis |
| 2,086,701 | A | 7/1937 | Dreyfus |
| 3,743,572 | A | 7/1973 | Richter et al. |
| 4,055,673 | A | 10/1977 | Mueller et al. |

(Continued)

FOREIGN PATENT DOCUMENTS

| CA | 1070537 | 1/1980 |
|---|---|---|
| CA | 1147105 A | 5/1983 |

(Continued)

OTHER PUBLICATIONS

Schell et al., Dilute-sulfuric acid pretreatment of corn stover in pilot-scale reactor, 2003, Humana Press Inc., vol. 105, No. 1-3, pp. 69-85.*

(Continued)

*Primary Examiner* — David C Mellon
(74) *Attorney, Agent, or Firm* — Philip C. Mendes da Cost; Bereskin & Parr LLP/S.E.N.C.R.L., s.r.l.

(57) ABSTRACT

A method and apparatus for pre-treating a cellulosic feedstock are disclosed. Embodiments of the method comprise conveying the cellulosic feedstock through an enclosed volume, adding moisture to the cellulosic feedstock simultaneously at multiple spaced-apart moisture injection points as the cellulosic feedstock travels through the volume, and heating the cellulosic feedstock as it travels through the volume to obtain a heated moistened feedstock. Embodiments of the apparatus comprise a shell defining a treatment chamber having a lower inner surface. The treatment chamber has an inlet and an outlet spaced longitudinally apart from the inlet to define an axial length. A conveyance member is housed within the shell and is configured to sweep the lower inner surface. A plurality of injection ports are provided in at least one of the shell and the conveyance member.

19 Claims, 8 Drawing Sheets

U.S. PATENT DOCUMENTS

| | | | |
|---|---|---|---|
| 4,062,304 A | | 12/1977 | Herbold et al. |
| 4,119,025 A | | 10/1978 | Brown |
| 4,136,207 A | | 1/1979 | Bender |
| 4,160,695 A | | 7/1979 | Dietrichs et al. |
| 4,181,796 A | | 1/1980 | Dietrichs et al. |
| 4,186,658 A | | 2/1980 | Brown |
| 4,211,163 A | | 7/1980 | Brown et al. |
| 4,281,934 A | | 8/1981 | Krause |
| 4,286,884 A | * | 9/1981 | Retrum .................. 366/149 |
| 4,316,748 A | * | 2/1982 | Rugg et al. .................. 127/37 |
| 4,364,667 A | | 12/1982 | Reiner |
| 4,412,485 A | | 11/1983 | Brown |
| 4,427,453 A | * | 1/1984 | Reitter .................. 127/1 |
| 4,483,625 A | | 11/1984 | Fisher et al. |
| 4,600,590 A | * | 7/1986 | Dale .................. 426/69 |
| 4,676,363 A | | 6/1987 | Buchmuller et al. |
| 4,775,239 A | | 10/1988 | Martinek et al. |
| 4,798,651 A | | 1/1989 | Kokta |
| 4,867,846 A | | 9/1989 | Fleck |
| 4,911,558 A | | 3/1990 | Teske |
| 4,947,743 A | | 8/1990 | Brown et al. |
| 4,997,488 A | * | 3/1991 | Gould et al. .................. 127/37 |
| 5,023,097 A | | 6/1991 | Tyson et al. |
| 5,114,488 A | * | 5/1992 | Huber et al. .................. 127/1 |
| 5,122,228 A | | 6/1992 | Bouchette et al. |
| 5,338,366 A | | 8/1994 | Grace et al. |
| 5,791,779 A | | 8/1998 | Smith |
| 5,863,389 A | | 1/1999 | White et al. |
| 6,419,788 B1 | | 7/2002 | Wingerson |
| 6,423,145 B1 | | 7/2002 | Nguyen et al. |
| 6,498,029 B2 | | 12/2002 | Keller, Jr. et al. |
| 6,572,734 B2 | | 6/2003 | Baker |
| 6,660,506 B2 | | 12/2003 | Nguyen et al. |
| 2003/0089465 A1 | * | 5/2003 | Schaible et al. .................. 162/19 |

FOREIGN PATENT DOCUMENTS

| | | |
|---|---|---|
| CA | 1173825 | 9/1984 |
| CA | 1190923 | 7/1985 |
| CA | 1267407 | 3/1990 |
| CA | 1287705 | 8/1991 |
| CA | 2037275 A1 | 8/1992 |
| CA | 2063547 A1 | 9/1993 |
| CA | 2065939 A1 | 10/1993 |
| CA | 2339002 A1 | 7/1999 |
| CA | 2638150 A1 | 1/2010 |
| EP | 0487793 A1 | 6/1992 |
| FR | 777824 | 3/1935 |
| GB | 1043460 A | 9/1966 |
| WO | 2005079190 A2 | 9/1995 |
| WO | WO 2006055362 A1 * | 5/2006 |
| WO | 2007009463 A2 | 1/2007 |
| WO | 2010006840 A2 | 1/2010 |

OTHER PUBLICATIONS

Q.A. Nguyen et al., "NREL/DOE Ethanol Pilot-Plant: Current Status and Capabilities" (1996) 58 Bioresource Technology 189.

R.P. Overend & E. Chornet, "Fractionation of lignocellulosics by steam-aqueous pretreatments" (1987) 321 Phil. Trans. R. Soc. Lond. A. 523.

D. Ballerini et al., "Ethanol Production from Lignocellulosics: Large Scale Experimentation and Economics" (1994) 50 Biousource Technology 17.

K.M.F. Kazi, P. Jollez, & E. Chornet, "Preimpregnation: An Important Step for Biomass Refining Processes" (1998) 15:2 Biomass and Bioenergy 125.

M.P. Tucker et al., "Comparison of Yellow Poplar Pretreatment Between NREL Digester and Sunds Hydrolyzer" (1998) 70-72 Applied Biochemistry and Biotechnology 25.

Charles E. Wyman et al., "Comparative Sugar Recovery Data from Laboratory Scale Application of Leading Pretreatment Technologies to Corn Stover" (2005) 96 Bioresource Technology 2026.

Charles E. Wyman et al., "Coordinated Development of Leading Biomass Pretreatment Technologies" (2005) 96 Bioresource Technology 1959.

Nathan Mosier et al., "Features of Promising Technologies for Pretreatment of Lignocellulosic Biomass" (2005) 96 Biosource Technology 673.

Tim Eggeman & Richard T. Elander, "Process and Economics Analysis of Pretreatment Technologies" (2005) 96 Bioresource Technology 2019.

Abengoa Bioenergy, Press Release, "Abengoa Bionergy Awarded DOE Financial Assistance Agreement" (Feb. 28, 2007), online: Abongoa Bioenergy <http://www.abengoabioenergy.es/corp/web/en/acerca_de/sala_de_prensa/historico/2007/20070228_noticias.html#>.

Outputs from the EPOBIO Workshop, Greece, "Products from Plants—From Crops and Forests to Zero Waste Biorefineries" (May 15-17, 2007).

Abengoa Bioenergy, Press Release, "Abengoa Bionergy Opens Pilot Plant for the Energy of the Future" (Oct. 15, 2007), online: Abengoa Bioenergy <http://www.abengoabioenergy.es/corp/web/en/acerca_de/sala_de_prensa/historico/2007/20071015_noticias.html#>.

Merrick & Company, Final Report of Jun. 14, 1999, "Softwood Biomass to Ethanol Feasibility Study" (Aug. 2004) Subcontractor Report published by National Renewable Energy Laboratory.

Merrick & Company, Final Report of Jan. 2000, "Building a Bridge to the Corn Ethanol Industry. Corn Stover to Ethanol at High Plains Corporation's York, Nebraska Co-Located Plant Site".

Melvin P. Tucker et al., "Conversion of Distiller's Grain into Fuel Alcohol and a Higher-Value Animal Feed by Dilute-Acid Pretreament" (2004) 113-116 Applied Biochemistry and Biotechnology 1139.

Melvin P. Tucker et al., "Effects of Temperature and Moisture on Dilute-Acid Steam Explosion Pretreatment of Corn Stover and Cellulase Enzyme Digestibility" (2003) 105-108 Applied Biochemistry and Biotechnology 165.

Kyoung Heon Kim et al., "Continuous Countercurrent Extraction of Hemicellulose from Pretreated Wood Residues" (2001) 91-93 Applied Biochemistry and Biotechnology 253.

Quang A. Nguyen et al., "Two-Stage Diute-Acid Pretreatment of Softwoods" (2000) 84-86 Applied Biochemistry and Biotechnology 561.

Daniel J. Schell et al., "Dilute-Sulfuric Acid Pretreatment of Corn Stover in Pilot-Scale Reactor" (2003) 105-108 Applied Biochemistry and Biotechnology 69.

Q.A. Nguyen & J.N. Saddler, "An Integrated Model for the Technical and Economic Evaluation of an Enzymatic Biomass Conversion Process" (1991) 35 Bioresource and Technology 275.

Q.A. Nguyen et al., "Dilute Acid Pretreatment of Softwoods", Scientific Note, (1998) 70-72 Applied Biochemistry and Biotechnology 77.

Q.A. Nguyen et al., "Dilute Acid Hydrolysis of Softwoods", Scientific Note, (1999) 77-79 Applied Biochemistry and Biotechnology 133.

Raphael Katzen & Donald F. Othmer, "Wood Hydrolysis. A Continuous Process" (1942) 34 Industrial and Engineering Chemistry 314.

"Transactions of the Institution of Chemical Engineers" (1993) 11 Institution of Chemical Engineers, London, the United Kingdom.

Diane Knappert, Hans Grethlein & Alvin Converse, "Partial Acid Hydrolysis of Cellulosic Materials as a Pretreatment for Enzymatic Hydrolysis" (1980) 22 Biotechnology and Bioengineering 1449.

Sung Bae Kim & Y.Y. Lee, "Diffusion of Sulfuric Acid within Lignocellulosic Biomass Particles and its Impact on Dilute-Acid Pretreatment" (2002) 83 Bioresource Technology 165.

Alan W. Roberts, "Design Considerations and Performance Evaluation of Screw Conveyors", online: The South African Institute of Materials Handling <http://www.saimh.co.za/beltcon/beltcon11/beltcon1114.htm>.

National Renewable Energy Laboratory, "Process Design and Cost Estimate of Critical Equipment in the Biomass to Ethanol Process. Acid Hydrolysis Reactors Batch Systems", Report (Seattle, Washington: Harris Group Inc., 2001).

Osamu Kitani & Carl W.. Hall, eds., "Biomass Handbook" 470-474 (Gordon and Breach Science Publishers: New York).

Buell Classifier Fisher-Klosterman, Leaflet, "Operation Principles and Efficiency".

Process Sensors Corporation, "On-Line Moisture Measurement and Control Manufacturing Industries Worldwide", Product Information, online: Process Sensors Corporation <http://processsensors.com/index.html? gclid=CKT27fXvJ0CFREWagodclkUcw>.

Roger M. Rowell, Raymond A. Young, & Judith K. Rowell, eds., Paper and Composites from Agro-Based Resources (Lewis Publishers).

G.H.Emert et al., "Gasohol/Biomass Developments: Economic Update of the Gulf Cellulose Alcohol Process" (Sep. 1980) Chemical Engineering Progress 47.

Ron Kotrba, "The Project of a Lifetime" (Feb. 2006), Ethanol Producer Magazine.

National Renewable Energy Laboratory, "Research Advances: NREL Leads the Way. Cellulosic Ethanol", Brochure, (Mar. 2007), online: National Renewable Energy Laboratory <http://www.nrel.gov/biomass/pdfs/40742.pdf>.

National Renewable Energy Laboratory, Fact Sheet, "Clean Cities: Ethanol Basics" (Oct. 2008), online: U.S. Department of Energy <www.afdc.energy.gov/afdc/pdfs/43835.pdf>.

Brent D. Yacobucci, "Fuel Ethanol: Background and Public Policy Issues", (Mar. 3, 2006), CRS Report for Congress, online: U.S. Department of State, Foreign Press Centre <fpc.state.gov/documents/organization/62837.pdf>.

U.S. Department of Energy, Energy Efficiency & Renewable Energy, Alternative Fuels & Advanced Vehicles Data Center, Article, "Ethanol Market Penetration", online: U.S Department of Energy <http://www.afdc.energy.gov/afdc/ethanol/market.html>.

Kenneth W.Britt, ed., "Handbook of Pulp and Paper Technology", 2nd. ed. (New York: Van Nostrand Reinhold Company).

A. Aden et al., "Lignocellulosic Biomass to Ethanol Process Design and Economics Utilizing Co-Current Dilute Acid Prehydrolysis and Enzymatic Hydrolysis for Corn Stover", (Jun. 2002), Technical Report published by National Renewable Energy Laboratory.

U.S. Department of Energy Office of Science, Genomics Science Program, "Fuel Ethanol Production", online: U.S. Department of Energy Office of Science <http://genomicscience.energy.gov/biofuels/ethanolproduction.shtml>.

Metso Automation, Metso Automation's Newsletter for Neles and Jamesbury products, "Biofuels—a growth market for Metso", (Summer 2008), online: Metso <http://valveproducts.metso.com/metsoautomation/DocDB/catalogs/catalog.taf?pg_parent=397>.

SunOpta Inc., News Release, "SunOpta Announces Sale of Cellulosic Ethanol Facility to China Resources Alcohol Corporation", (Jun. 23, 2006), online: SunOpta Inc. <http://investor.sunopta.com/releasedetail.cfm? ReleaseID=287111>.

Ralph P. Overend, Slideshow, "The Lignocellulosic bottleneck: material properties, architecture and pretreatment".

Robert Wooley et al., "Lignocellulosic Biomass to Ethanol Process Design and Economics Utilizing Co-Current Dilute Acid Prehydrolysis and Enzymatic Hydrolysis Current and Futuristic Scenarios", (Jul. 1999), National Renewable Energy Laborator. Technical Report.

Nathan S. Masier, "Cellulosic Ethanol—Biofuel Beyond Corn" Bio Energy, Purdue University.

U.S Securities and Exchange Commission, "Annual Report Under Section 13 or 15(d) of the Securities Exchange Act of 1934", for Bluefire Ethanol Fuels, Inc. Signed on Feb. 28, 2008.

U.S Securities and Exchange Commission, "Annual Report Under Section 1 or (15)d of the Securities Exchange Act of 1934", for CleanTech Biofuels, Inc. Signed on Mar. 28, 2008.

Office Action on co-pending Canadian Application 2,638,152 dated Feb. 8, 2011.

Abengoa Bioenergy New Technologies Inc. f/k/a *Abengoa Bioenergy R&D, Inc.* v. *Mascoma Corporation*; Notice of Arbitration and Statement of Claim, submitted to American Arbitration Association Commercial Arbitration Tribunal on Nov. 2, 2011, pp. 1-14.

International Search Report received on the corresponding international application No. PCT/CA2009/001032, dated Oct. 27, 2009.

International Search Report received on the corresponding international application No. PCT/CA2009/001035, dated Nov. 5, 2009.

Brownell et al., "Steam-Explosion Pretreatment of Wood: Effect of Chip Size, Acid, Moisture Content and Pressure Drop", Biotechnology and Bioengineering, vol. 28 pp. 792-801 (1986).

Cullis et al. Effect of Initial Moisture Content and Chip Size on the Bioconversion Efficiency of Softwood Lignocellulosics; Biotechnology and Bioengineering, vol. 85, No. 4, pp. 413-421, (2004).

Duff et al., "Bioconversion of forest products industry waste cellulosics to fuel ethanol: A review", Bioresource Technology, vol. 5 pp. 1-33 (1996).

Written Opinion of the International Searching Authority, dated Oct. 8, 2010, corresponding to International application No. PCT/CA2010/001091.

PCT International Search Report, dated Oct. 8, 2012, corresponding to International application No. PCT/CA2010/001091.

* cited by examiner

FIG.5A

METHOD AND APPARATUS FOR TREATING A CELLULOSIC FEEDSTOCK

FIELD

The invention relates to a method and apparatus for preparing a cellulosic feedstock for the subsequent production of a fermentable sugar stream from the cellulose and hemicellulose in the cellulosic feedstock wherein the fermentable sugar stream may be used for subsequent ethanol production. More specifically, the invention relates to a method and apparatus for treating a cellulosic feedstock by moistening and heating the cellulosic feedstock.

BACKGROUND

Several processes for the production of ethanol are known. Generally, the production of fuel ethanol involves the fermentation of sugars with yeast. Typically, the sugars are derived from grains, such as corn and wheat. The starches in the grains are subjected to enzymatic hydrolysis in order to produce the sugars, which are then subjected to fermentation to produce ethanol.

Plant materials are a significant source of fermentable sugars, such as glucose that can be transformed into biofuels. However, the sugars in plant materials are contained in long polymeric chains of cellulose and hemicellulose. Utilizing current fermentation processes, it is necessary to break down these polymeric chains into monomeric sugars, prior to the fermenting step.

Recently, processes have been developed for utilizing plant materials, such as corncobs, straw, and sawdust, to produce sugars for ethanol fermentation. Such processes typically comprise pre-treating the feedstock to increase the accessibility of the cellulose to hydrolysis enzymes, and subjecting the cellulose to cellulase enzyme systems to convert the cellulose into glucose.

Methods of converting plant biomass into fermentable sugars are known in the art and in general comprise two main steps: a pre-treatment step to activate the plant structure, and an enzymatic or chemical hydrolysis step to convert the polymeric chains of cellulose and hemicellulose into monomeric sugars. Several approaches have been used for the pre-treatment step, e.g., autohydrolysis, acid hydrolysis, ammonia activation, kraft pulping, organic solvent pulping, hot water pre-treatment, ammonia percolation, lime pre-treatment, caustic soda pulping, or alkali peroxide pre-treatment. Early pre-treatment steps included grinding or milling the feedstock into a powder, which was then mixed with water to form a slurry.

More recently, solvent based pre-treatments, alkali pre-treatments, and acidic pre-treatments have also been described. PCT publication WO/2007/009463 to Holm Christensen describes an alternate pre-treatment, which does not involve the addition of acids, bases, or other chemicals. This pre-treatment process involves soaking the cellulosic material in water, conveying the cellulosic material through a heated and pressurized reactor, and pressing the cellulosic material to produce a fiber fraction and a liquid fraction. During the soaking step, approximately 2.5-3.5 kg of liquid per 1 kg of fiber is added, and is removed again during pressing. The overall pre-treatment process can take about 27 minutes.

Each pre-treatment technology has a different mechanism of action on the plant structure, inducing either physical and/or chemical modifications. However, the main objective of the pre-treatment is to provide accessibility of the plant material to the enzymes.

SUMMARY

The commercial viability of a hydrolysis process is dependent on the character of the feedstock provided to the hydrolysis unit. Typically, this requires that a feedstock is activated such that a significant portion (e.g., greater then 75%) of the cellulose and hemicellulose of the feedstock is accessible to hydrolysis enzymes. If such an activated feedstock is provided to an enzymatic hydrolysis unit, then at least 60%, preferably more than 75% and more preferably over 90% of the cellulose and hemicelluloses may be converted to monomeric sugars. This sugar rich process stream may subsequently be subjected to fermentation to produce an alcohol stream. The alcohol stream from the fermentation stage (i.e., the raw alcohol stream) may have an ethanol content of about 3-22% v/v, preferably about 5-15% and more preferably more about 8-12%.

An activated feedstock for enzymatic hydrolysis is preferably prepared by autohydrolysis, which is preferably conducted in a steam explosion reactor also known as a hydrolyzer, (also known as a digester). Autohydrolysis is a process of breaking down hemicellulose and cellulose by exposure to high temperatures, steam and pressure. When performed in the presence of an added acid, the reaction is known as acid hydrolysis.

During autohydrolysis, the degree of polymerization of cellulose may be reduced from about 10,000 to about 1,500-1,000. This process is preferably carried out above the glass transition temperature of lignin (120-160° C.). Depending upon the severity of the reaction, degradation products may be produced, such as furfural, hydroxyl-methylfurfural, formic acid, levulinic acid and other organic compounds.

During a steam explosion treatment (more commonly called autohydrolysis if no externally added catalyst), a cellulosic feedstock is subjected to elevated heat (e.g., 180° C. to 220° C.) and pressure (e.g., 131 psig to 322 psig) optionally in the presence of suitable chemicals (e.g., organic/ and/or inorganic acids, ammonia, caustic soda, sulfur dioxide, solvents etc.) in a pressurized vessel. Preferably, external chemical addition is not utilized, in which case, the only catalyst that may be present may be acetic acid that is generated in situ. The treated cellulosic feedstock is then released from the pressurized vessel such that the pressure is rapidly reduced (e.g., 1 second or less). The biomass may exit the hydrolyzer into a reduced pressure, preferably atmospheric pressure and, more preferably into a vacuum. The rapid decrease in pressure results in the biomass separating into individual fibers or bundles of fibers. This step opens the fiber structure and increases the surface area. The lignin remains in the fiber along with cellulose and residual hemicellulose. Accordingly, the explosive release of pressure, combined with the high temperature and pressure treatment results in the physico-chemical modification of the cellulosic feedstock that is then suitable for feeding to an enzymatic hydrolysis unit.

In order for the steam explosion process to be able to produce an activated feedstock that is capable of producing such a sugar rich process stream, the temperature and moisture level of the cellulosic feedstock that is fed to a steam explosion reactor preferably is relatively uniform and preferably has a temperature from about 50 to about 70° C., and more preferably 50-65° C., and a moisture content from about 30 to 60 wt % (preferably 45 to about 55 wt %).

Without being limited by theory, it is believed that an unexpected increase in the conversion of the feedstock to fermentable sugars may be achieved if the moisture content of the feedstock fed to the steam explosion reactor is lower, provided that sufficient water is present for hydrolyzing and/or activating the feedstock. If the feedstock is too dry, then there may be insufficient water molecules present in the fiber and hence not all of the feedstock will be activated and/or hydrolyzed (i.e., the hydrolysis reaction/activation will not occur at all possible sites). Accordingly, it might be presumed that a substantial excess of water should be used to ensure water molecules are available at each hydrolysis/activation site. Surprisingly, it has been determined that if the cellulosic feedstock that is fed to a steam explosion reactor has an excess of moisture, then a smaller percentage of the available sites of the feedstock are activated and/or hydrolyzed than would be expected. It is believed that this is due to the high moisture content acting as a barrier to heat transfer through the fiber structure. The external fiber reaches the process temperature far in advance to the internal fiber, hence resulting in very uneven heat transfer and the resulting uneven autohydrolysis reaction. Further, during the autohydrolysis process additional water may be provided to the process by way of direct injected steam in order to raise the fiber temperature from the inlet temperature to the outlet temperature of the reactor. If the inlet moisture content of the fiber is at saturation, then the additional water will be free water in the autohydrolysis reactor resulting in washing of the soluble hemicellulose from the fiber and causing subsequent accumulation of hemicellulose within the reactor. Over time, the accumulated hemicellulose will tend to break down to inhibitor compounds and deposit degraded sugars on the internal components of the reactor. These deposits will become and obstruction to the flow of the biomass.

It has also been determined that if the cellulosic feedstock that is fed to a hydrolyzer has a temperature that is too high, then some percentage of the hemicellulose sugars will be degraded to inhibitory compounds prior to starting the autohydrolysis reaction and further amounts during the autohydrolysis reaction itself. Conversely, if the fiber is too cold entering the hydrolyzer, the first one third to one half of the reactor vessel may act as a preheating device rather than as a hydrolyzer, resulting in incomplete autohydrolysis. Accordingly, it is preferred to have very consistent fiber temperature year round as well as from night to day time operation, for the fiber that is fed to the hydrolyzer reactor. Further, it is preferred that the fiber in the feedstock fed to the autohydrolysis unit have a relatively uniform temperature profile. For example, it is preferred that the core of the blocks of material have a temperature that is within 80%, preferably 90% of the temperature of the exterior surface of the material. Accordingly, for example, if the temperature of the exterior surface of the material is from 50 to 70° C., then the temperature of the core of the material is preferably from 45 to 63° C.

It has also been determined that the fiber requires time for the moisture that is added to become equilibrated throughout the entire fiber particle. It has been determined that under laboratory conditions, it may take from 5 to 9 minutes to equilibrate the moisture content of the fiber. Under industrial conditions it will be longer. Preferably, the autohydrolysis reaction time in the vessel is typically about 5 to 6 minutes or less. It is preferred that the fiber in the feedstock fed to the autohydrolysis unit have a relatively uniform moisture profile. For example, it is preferred that the core of the blocks of material have a moisture content that is within 80%, preferably 90% of the moisture content of the exterior surface of the material. Accordingly, for example, if the moisture content of the exterior-surface of the material is from 45 to 55 wt %, then the moisture content of the core of the material is preferably from 40.5 to 49.5 wt %.

Accordingly, embodiments of the present invention relate to a cellulosic feedstock pre-treatment process, which comprises the addition of moisture to a cellulosic feedstock, while mixing the feedstock, to prepare the feedstock for hydrolysis. Subsequent to this soaking or impregnation stage, it is preferred to subject the feedstock to an autohydrolysis reaction.

In one broad aspect, a method is provided for treating a cellulosic feedstock, such as for subsequent ethanol production. The method comprises conveying the cellulosic feedstock through an enclosed volume. The method further comprises adding moisture to the cellulosic feedstock simultaneously at multiple spaced-apart moisture injection points as the cellulosic feedstock travels through the volume, and heating the cellulosic feedstock as it travels through the volume to obtain a heated moistened feedstock. In some embodiments, the heated moistened feedstock is subsequently subjected to hydrolysis, preferably autohydrolysis followed by enzymatic hydrolysis.

In some embodiments, the volume comprises an impregnation chamber defined by chamber walls having an inner surface, and the impregnation chamber extends longitudinally along an axial length from an intake to an outlet, and the cellulosic feedstock is urged through the chamber by a conveyance member.

In some embodiments, the step of adding moisture comprises adding moisture to increase the moisture content of the cellulosic feedstock from about 5-15 wt % to about 45-55 wt %. In some embodiments, the method further comprises adding heated water as at least part of the moisture. In some embodiments, the method further comprises adding a catalyst with the moisture. Preferably, the heated water is at a temperature up to 70° C. and preferably about 50-60° C.

In some embodiments, the step of heating the cellulosic feedstock comprises heating the cellulosic feedstock from less than about 30° Celsius at the inlet, to at least about 65° Celsius at the outlet.

In some embodiments, the plurality of injection points comprises a plurality of ports extending through the chamber wall commencing proximate the inlet and the method further comprising introducing moisture to the cellulosic feedstock at least during its initial travel through the impregnation chamber. In some further embodiments, the injection points are provided in a first third of the axial length of the impregnation chamber.

In some embodiments, the step of heating the cellulosic feedstock comprises heating the cellulosic feedstock to about 50-70° Celsius at the outlet. In some embodiments, the step of heating the cellulosic feedstock comprises heating the moisture prior to contacting the moisture with the feedstock.

In some embodiments, the step of heating the cellulosic feedstock comprises indirectly heating the cellulosic feedstock by heating at least one of the chamber walls and the conveyance member.

In some embodiments, the conveyance member extends longitudinally through the impregnation chamber and is configured to urge the cellulosic feedstock axially through the impregnation chamber as the conveyance member rotates.

In some embodiments, the conveyance member comprises a rotary shaft extending longitudinally through the impregnation chamber and a plurality of paddles extending radially outwardly from the shaft, and the method further comprises rotating the shaft to urge the cellulosic feedstock axially through the impregnation chamber.

In some embodiments, the conveyance member includes moisture injection points, and the method further comprises introducing moisture to the volume as the conveyance member rotates.

In some embodiments, the conveyance member includes a fluid conduit extending longitudinally through the shaft and a plurality of paddle ducts in communication with the fluid conduit and extending through the paddle to an outer surface thereof, and the step of adding moisture to the cellulosic feedstock comprises injecting moisture into the feedstock through the paddle ducts.

In some embodiments, the conveyance member comprises a rotary shaft extending longitudinally through the impregnation chamber, and a plurality of paddles extending radially outwardly from the shaft, and the paddles are configured relative to the impregnation chamber to sweep at least a lower circumferential portion of the inner surface of the chamber walls when the feedstock is conveyed through the chamber.

In some embodiments, the conveyance member comprises a rotary shaft extending longitudinally through the impregnation chamber and a plurality of paddles extending radially outwardly from the shaft and the paddles are spaced and configured such that the lower circumferential portion of the chamber is swept along generally the entire axial length of the chamber as the feedstock is conveyed through the chamber.

In some embodiments, the volume has a residence time of less than about ten minutes. Such embodiments may be advantageous because the process may be substantially fast, and may prevent overheating of the fibers, thereby preventing degradation of the fibers.

In some embodiments, the method further comprises monitoring the moisture content of the feedstock and introducing an amount of moisture to produce a predetermined moisture content of the heated moistened feedstock.

In some embodiments, the method further comprises providing a feedstock comprising cellulosic material that has a moisture content of less than about 50 wt % and comprises fibers that have a length in the range of about 4 mm to about 7 mm. More preferably, the feedstock comprises a moisture content from 5 to 45 wt % and more preferably from 10 to 30 wt %.

In some embodiments, the method further comprises subsequently subjecting the cellulosic feedstock to a downstream hydrolysis process.

In another broad aspect, an apparatus for treating a cellulosic fiber feedstock is provided. The apparatus comprises a shell defining a treatment chamber having a lower inner surface. The treatment chamber has an inlet and an outlet spaced longitudinally apart from the inlet to define an axial length. A conveyance member is housed within the shell and is configured to sweep the lower inner surface. A plurality of injection ports are provided in at least one of the shell and the conveyance member.

In some embodiments, the plurality of injection ports comprises about 1 to 20 injection ports.

In some embodiments, the plurality of injection ports are positioned along at least a first portion of the axial length of the shell, wherein the first portion extends from the inlet towards the outlet.

In some embodiments, the conveyance member comprises at least a first rotary shaft and a plurality of paddles joined to the first shaft and extending radially outwardly therefrom.

In some embodiments, the paddles and the lower inner surface are configured to maintain a minimum space between the paddles and the lower inner surface of less than 6.5 mm.

In some embodiments, the paddles comprise blades, and the blades are generally planar members, having a radially inner edge attached to a stem, a radially outer edge opposite the radially inner edge, and opposing first and second side edges extending between the radially inner and outer edges. The radially outer edge may be curved to match an arc swept by the outer edge when the first shaft rotates.

In some embodiments, each blade is canted, wherein the first side edge is axially nearer the outlet and rotationally trailing relative to a second side edge.

In some embodiments, axially adjacent paddles extend from the shaft at different angular positions around to the shaft axis.

In some embodiments, the first side edge of one paddle axially overlaps the second side edge of a next adjacent paddle.

In some embodiments, the conveyance member comprises a second shaft, spaced transversely apart from and extending generally parallel to the first shaft and the lower inner surface is scallop shaped in transverse section.

In some embodiments, the conveyance member comprises a second shaft, spaced transversely apart from and extending generally parallel to the first shaft, each shaft has a plurality of paddles attached thereto, and the lower inner surface has a first portion below the first shaft and a second portion below the second shaft wherein, when viewed in transverse cross section, the first portion defines an arc at a constant distance to the first shaft and the second portion defines an arc at a constant distance to the second shaft.

In some embodiments, the second shaft rotates in an opposite direction to the first shaft.

In some embodiments, the apparatus further comprises a first heated fluid supply in fluid communication with the injection ports. In some embodiments, the first heated fluid supply comprises water heated to a temperature from about 60 to about 70° C. In some embodiments, the first heated fluid supply comprises a catalyst.

In some embodiments, the apparatus further comprises a jacket surrounding at least a portion of the shell and defining an enclosure between the jacket and the shell. In some embodiments, the apparatus further comprises a second heated fluid supply associated with the enclosure. In some embodiments, the second heated fluid supply comprises steam.

In some embodiments, the shaft comprises a conduit extending longitudinally therethrough. In some further embodiments, the conveyance member includes injection ports. In yet further embodiments, at least one of the stem and the paddles comprise injection ports.

In some embodiments, the apparatus further comprises a moisture sensor that measures the moisture content of the cellulosic fiber feedstock and a controller operatively controlling an amount of moisture introduced through the injection ports. Accordingly, a predetermined moisture content of the cellulosic fiber feedstock is obtained at the outlet. In some embodiments, the moisture sensor is upstream of the inlet. In some embodiments, the predetermined moisture content of the cellulosic fiber feedstock is from 45 to 55 wt %.

An advantage of this process is that the temperature of the feedstock may be kept sufficiently low to prevent charring of the fibers. Charring of the fibers results in degradation of the sugars in the cellulose and hemicellulose. This degradation reduces the percentage of sugars that may be liberated for fermentation, thereby decreasing the possible yield of the process. Further, the degradation may produce by products that are undesirable in downstream process streams. Charring may be reduced or prevented by using a lower temperature water supply to the heating jacket of the treatment chamber, a lower temperature of the water that is used to provide moisture and/or by avoiding fibers being retained too long in contact with a heated wall of the treatment chamber. For example, if steam is not used to provide moisture to the fibers in the treatment chamber, but water at, e.g., 50-60° C. is used, the feedstock will be heated but will not be raised to a temperature at which degradation may occur.

BRIEF DESCRIPTION OF THE DRAWINGS

These and other advantages of the present invention will be more fully and particularly understood in connection with the following description of the preferred embodiments of the invention in which.

DETAILED DESCRIPTION

Embodiments of the present invention provide a method and apparatus for treating a cellulosic feedstock for subsequent ethanol production. The method and apparatus of the preferred embodiment serve to heat and moisten the cellulosic feedstock to obtain a relatively uniform temperature and moisture level of the feedstock, while reducing, and preferably essentially preventing, the charring or other degradation of the cellulose and hemicellulose during this heating stage. Accordingly, the method and apparatus provide a cellulosic feedstock, which is suitable for the production of a fermentation precursor stream. The cellulosic feedstock may be subsequently treated to liberate sugars in the cellulose and hemicellulose and produce a sugar stream that may then be subjected to fermentation to obtain a high yield alcohol stream. An embodiment of an apparatus of the present invention is shown in FIGS. 1-8. It will be appreciated that although the method is described with reference to apparatus 200 and vice versa, the method may be carried out with an alternate apparatus, and apparatus 200 may be used according to an alternate method. Furthermore, although the method is described as a continuous process, it will be appreciated that the method may be carried out as a semi-continuous or batch process.

The cellulosic feedstock treated according to the method and/or utilizing apparatus 200 may be preferably a lignocellulosic feedstock. A lignocellulosic feedstock is derived from plant materials. As used herein, a "lignocellulosic feedstock" refers to plant fiber containing cellulose, hemicellulose and lignin. In some embodiments, the feedstock may be derived from trees, preferably deciduous trees such as poplar (e.g., wood chips). Alternately or in addition, the feedstock may also be derived from agricultural residues such as, but not limited to, corn stover, wheat straw, barley straw, rice straw, switchgrass, sorghum, bagasse, rice hulls and/or corn cobs. Preferably, the lignocellulosic feedstock comprises agricultural residues and wood biomass, more preferably wood biomass and most preferably deciduous. The applicants contemplate other sources of plant materials comprising cellulose, hemicellulose and/or lignin, such as algae, for use in deriving cellulosic feedstocks and any of those may be used.

The lignocellulosic feedstock is preferably cleaned, e.g., to remove ash, silica, metal strapping (e.g., from agricultural products), stones and dirt. The size of the components of the lignocellulosic feedstock may also be reduced. The size of the components of the feedstock may be from about 0.05 to about 2 inches, preferably from about 0.1 to about 1 inch, and more preferably from about 0.125 to about 0.5 inches in length. For example, the cellulosic feedstock may comprise fibers, e.g., chopped straw, of a length of between about 4 mm and about 7 mm. Any process machinery that is able to crush, grind or otherwise decrease the particle size may be utilized.

Generally, when the cellulosic feedstock is provided, it will have an initial or starting moisture content. The initial moisture content may depend on numerous factors, such as the nature of the cellulosic feedstock, and any upstream storage conditions. In some embodiments, the initial moisture content is less than about 15 wt % and, preferably, from 5-15 wt %. In some embodiments, at least some moisture may be provided in advance of the apparatus.

The method comprises conveying the cellulosic feedstock through an enclosed volume. The enclosed volume may be of a variety of configurations. Referring to FIGS. 1-5, in the embodiment shown, chamber 204 of apparatus 200 comprises an enclosed volume 202. Chamber 204 may be referred to as an impregnation chamber, or a treatment chamber.

In the embodiment shown, chamber 204 is defined by a shell 206, which preferably is provided with a heating jacket 260. Accordingly, shell 206 preferably comprises an inner wall 208 and a spaced apart outer wall 209 defining a volume 207 therebetween. Accordingly, chamber 204 may be a double walled chamber having a volume 207 through which a heated fluid may be passed from, e.g., inlet to the volume 207 to the outlet from the volume. Wall 208 has an inner surface 210 that encloses chamber 204. It will be appreciated that a single walled vessel may be used. It will be appreciated that heating jacket 260 may surround only part of chamber 204 and may be of any design.

In some embodiments, an impregnator feeder 262, namely a feeder that conveys feedstock into chamber 204, is preferably positioned upstream of mixing or impregnation chamber 204. Feeder 262 may be of any design. Preferably, feeder 262 is of a design that inhibits, and preferably prevents, the flow of moisture upstream of feeder 262. For example, a rotating valve or the like may be provided to segment such upstream flow. Preferably impregnation feeder is a screw feeder comprising a motor 264 drivenly connected to a screw or auger 266 positioned below an inlet, such as via a transmission or gear reduction assembly provided in housing 268. The shaft on which screw 266 is provided may be rotatably mounted in housing 270 such that auger 266 is a cantilevered plug screw conveyor. Accordingly, feeder 262 produces a plug of material that prevents upstream migration of moisture. The plug may be conveyed into inlet housing 272 that is mounted, e.g., to outer wall 209 and positioned above inlet 211 to volume 202. The feedstock may then pass downwardly into chamber 204.

Chamber 204 comprises at least one feedstock inlet 211, and at least one treated feedstock outlet 213, which may be positioned above outlet passage 218. Inlet 211 and outlet 213 are spaced axially apart to define a length L. Length L may vary depending on the particular embodiment, however, in some embodiments, length L may be between about 8 ft and about 12 ft. In the embodiment shown, inlet 211 is defined in upper portion of shell 206, and outlet 213 is defined in lower portion of shell 206. Accordingly, the cellulosic feedstock is deposited into inlet 211, is conveyed along the length of chamber 204 and drops out of outlet 213 into optional outlet passage I218, which is upstream of optional heated holding tank 221. In alternate embodiments, inlet 211 and outlet 213 may be positioned elsewhere, for example at opposed ends of chamber 204.

In one aspect of the invention, chamber 204 may be of any configuration that provides a residence time for the feedstock to be treated (heated and/or provided with moisture) so as to obtain a treated feedstock having a moisture level and a temperature within a predetermined range, and which is preferably uniform for the feedstock exiting the chamber.

In one particularly preferred aspect, and preferably in combination with the forgoing aspect, the chamber and a conveyance member 222 are configured such that the feedstock is moved through the chamber with a relatively constant residence time. Preferably, the chamber and a conveyance member 222 are configured such that the lower surface on which the feedstock may rest under the influence of gravity is swept such that feedstock will be continually urged through the chamber.

Figure 1:
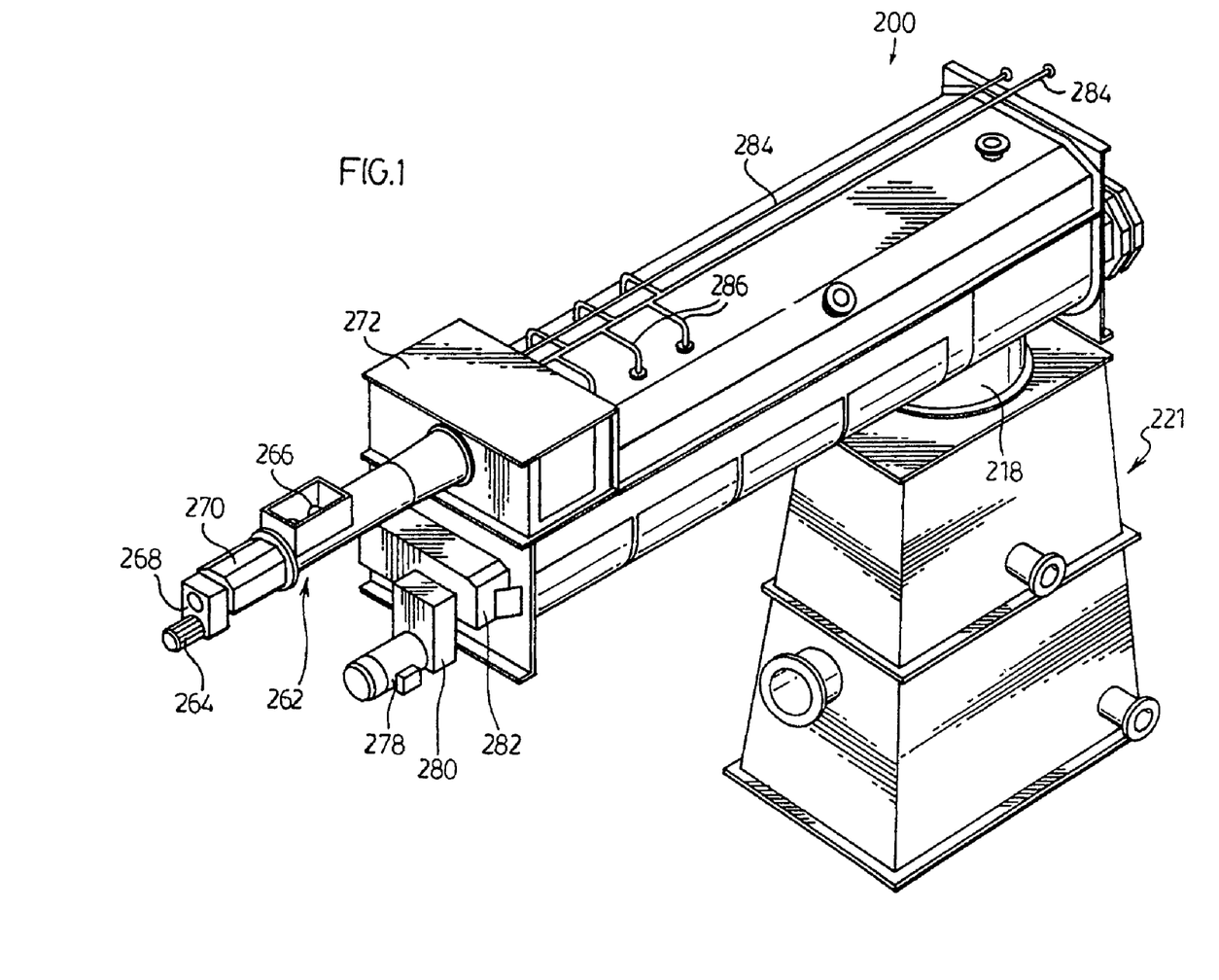
FIG. 1 is a perspective illustration of an embodiment of an apparatus of the present invention.
Figure 2:
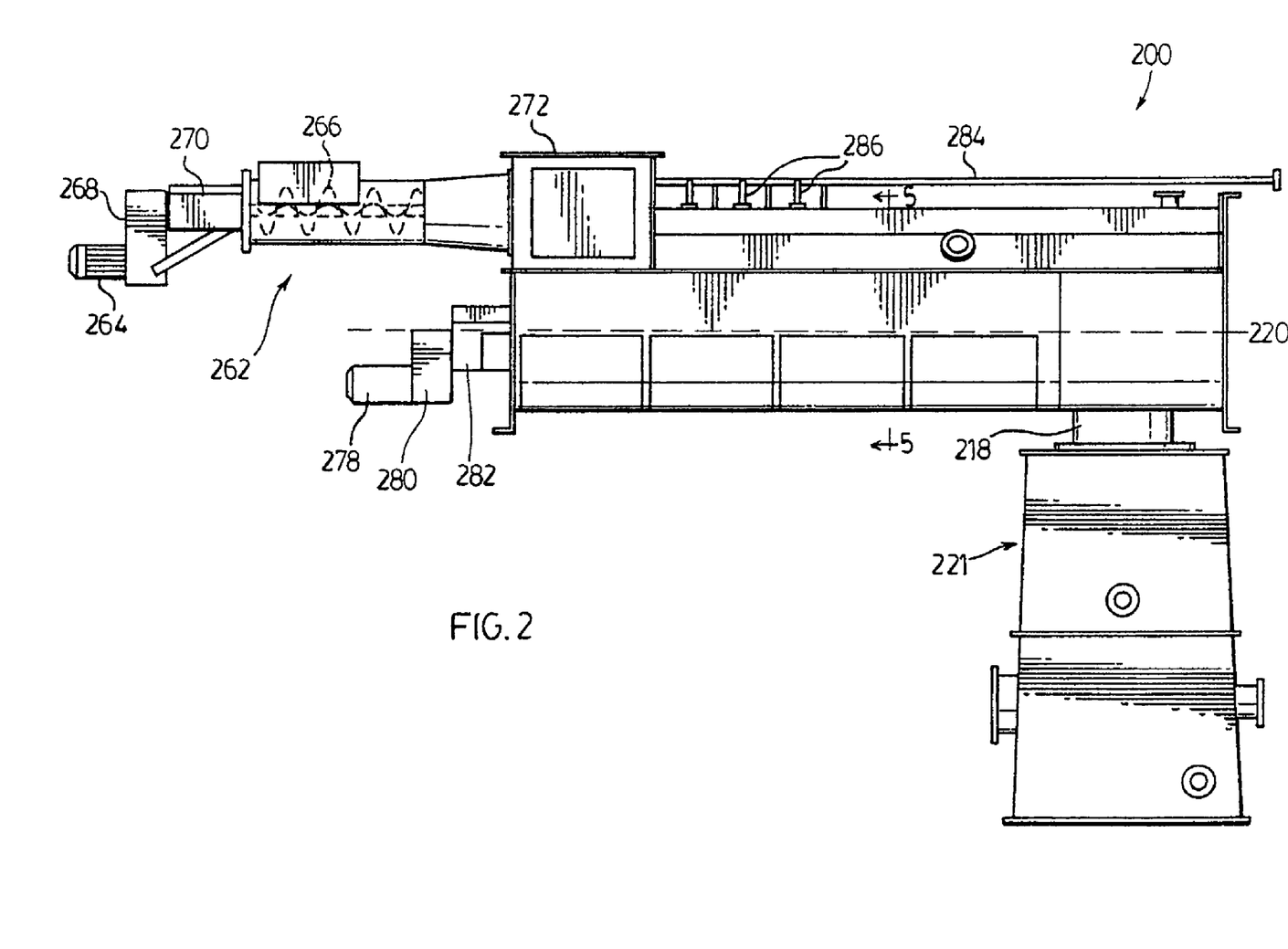
FIG. 2 is a front plan view of the apparatus of FIG. 1.
Figure 3:
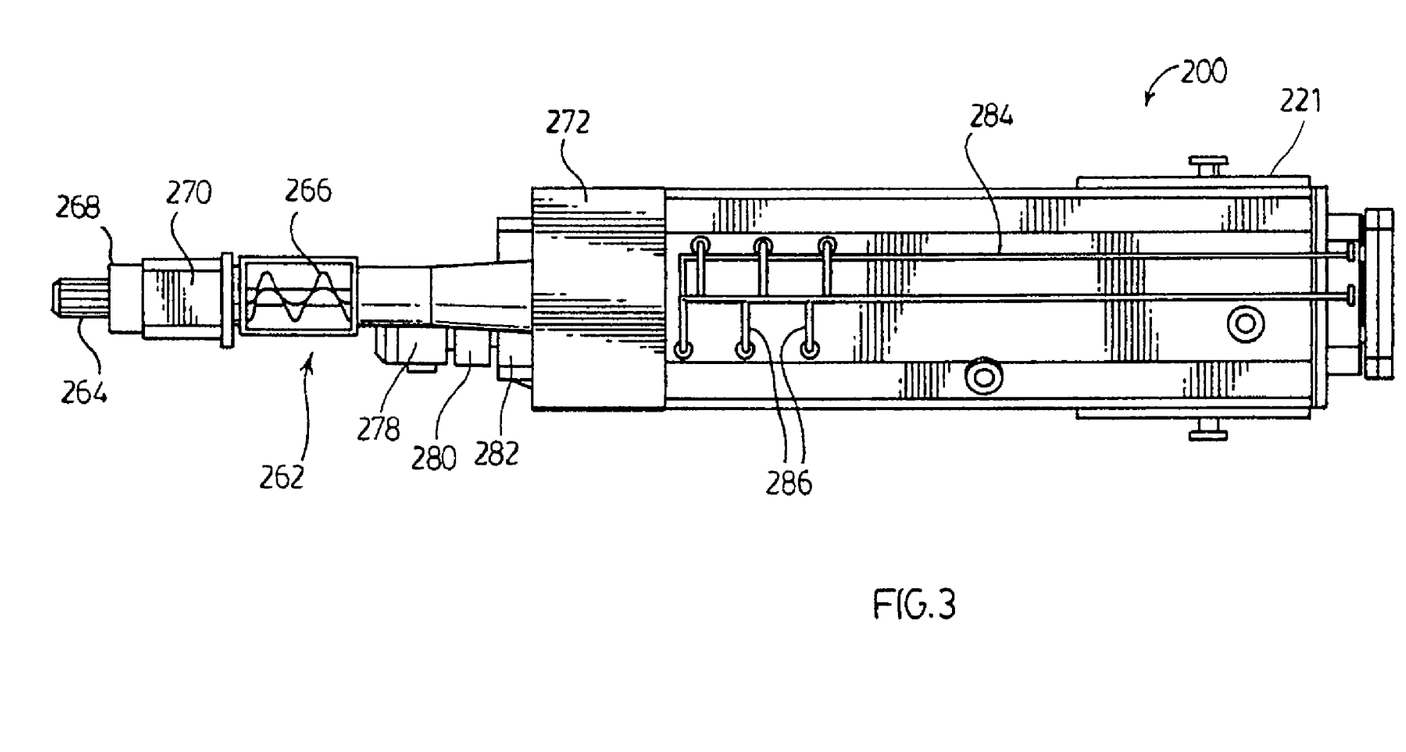
FIG. 3 is a top plan view of the apparatus of FIG. 1.

As exemplified in FIGS. 1-3, conveyance members 222 are rotatably mounted in chamber 204 and are drivenly connected to a motor 278. As exemplified, motor 278 is drivingly connected to conveyance members 222 via a transmission or gear reduction assembly provided in housing 280. The gear reduction assembly may be drivingly connected to ends 225, 227 of conveyance members 222 that are positioned inside housing 282.

In accordance with this particularly preferred aspect, chamber 204 extends longitudinally along axis 220 and has an upper portion that may be substantially cylindrical and a lower portion formed by wall section 214 that is preferably scallop shaped in transverse section (see FIGS. 6A and 6B). An advantage of having a scallop shaped lower section is that a rotary mounted conveyance member 222 may sweep adjacent all of, or at least much of, lower wall section 214 to reduce the likelihood of material having an increased residence time by not being conveyed along wall section 214. In alternate embodiments that are less preferred, chamber 204 may be otherwise shaped. For example, the upper portion may also be scallop shaped. Alternately, in combination with other aspect of this invention, the lower portion may be substantially cylindrical.

In accordance with this particularly preferred aspect conveyance member 222 is configured, in conjunction with the configuration of lower wall section 214, to urge the cellulosic feedstock through chamber 204 by sweeping lower wall section 214. That is, conveyance member 222 is preferably configured such that at least a portion thereof passes over lower inner surface in a continuous motion to push the cellulosic material forwardly. Furthermore, conveyance member 222 is preferably configured to sweep lower wall section 214 along generally the entire axial length of the chamber. It will be appreciated that, in less preferred embodiments, lower wall section 214 and conveyance member 222 need not be configured to sweep lower wall section 214 and may be of a variety of other configurations.

In the exemplified embodiments, in order to sweep lower wall section 214 and urge the cellulosic material through chamber 204, conveyance member 222 comprises first rotary shaft 224 and second rotary shaft 226, which extend longitudinally through chamber 204, and which are preferably spaced transversely apart and are preferably parallel. In alternate embodiments, conveyance member may comprise only one rotary shaft, or more than two rotary shafts.

Shafts 224, 226 may be provided with an auger, a plurality of paddles or the like. As exemplified, a plurality of paddles 228 extend radially outwardly from each rotary shaft. In addition, as exemplified in FIGS. 8A-8D, paddles 228 may each comprise a blade 232 and a stem 230, which couples the blade 232 to one of rotary shafts 226 and 228. Each blade 232 may be generally planar, and comprise a radially inner edge 234, a radially outer edge 236, and opposing first 238 and second 240 side edges, which extend between inner edge 234, and outer edge 236. In other embodiments, the paddles may be otherwise configured. For example, the blade may extend directly from the shaft, and a stem may not be provided. Alternatively, the stem may extend outwardly from the shaft, such that a space is provided between each blade and the shaft.

Blade 232 may be secured to one end of stem 230 by any means known in the art, such as welding, or mechanical affixation members such as rivets, or screws. The other end of stem 230 may be provided with a screw thread 276 on which bolt 274 may be received. Stem 230 may be secured to shaft 224, 226 such as by extending transversely through shaft 224, 226 from one side to the other and bolt 274 secured thereon. Suitable packing, gaskets or the like may be provided to limit or prevent moisture leaking out of shaft 224, 226 past stem 230. Stem 230 may be provided with one or more openings 258 in fluid communication with volume 256 inside shaft 224, 226. Accordingly, moisture may flow through shaft 224, 226, through stem 230 to paddle 228 and out through ports 252 into volume 204. However, paddles 228 may be directly secured to shafts 224, 226 or may be secured by any other means known in the art.

Preferably, as exemplified in FIG. 7, paddles 228 are arranged such that they generally define a longitudinally extending helix extending around each rotary shaft. In other words, a helix would be defined if the radially outer edge 236 of paddles were connected by a line extending from the inlet end of a rotary shaft to the outlet end thereof. Accordingly, helically adjacent paddles 228, for example paddles 228a and 228b, extend from the shaft at different angular positions around the shaft axis, as can be seen in FIG. 5.

Preferably, blades 232 of each paddle 228 are canted. That is, a first side edge 238 of each blade 232 is axially nearer the outlet 213 and rotationally trailing relative to a second side edge 240 (see FIG. 5).

Preferably, when viewed axially along the length of a rotary shaft, the first side edge of one paddle axially overlaps the second side edge of a next adjacent paddle.

In alternate embodiments, the paddles may be otherwise configured. For example, they may not be canted, and may be wedge shaped. Additionally, they may, for example, be arranged in a grid around shafts 226 and 224, rather than in a helix. It will be appreciated that in a particularly preferred embodiment, the paddles are arranged to define a helix, the blades are canted and the first side edge of one paddle axially overlaps the second side edge of a next adjacent paddle. However, these features may be used in any particular sub-combination with any aspect of this invention.

Accordingly, in the embodiment shown, the step of conveying the cellulosic feedstock through the enclosed volume 202 comprises rotating each shaft 224, 226, such that the paddles 228 engage the cellulosic feedstock and urge the cellulosic feedstock axially through the chamber 204. Furthermore, in this embodiment, when the rotary shafts 224, 226 rotate, paddles 228 pass over inner lower wall section 214 in a continuous motion to push the cellulosic material forwardly. An advantage of the exemplified design is that the outer radial edges of the blades are configured to travel a generally consistent distance above lower wall section 214, thereby being able to effectively sweep lower wall section 214.

It will be appreciated that, in alternate embodiments, conveyance member 222 may be otherwise configured. For example, conveyance member 222 may comprise an auger which extends along enclosed volume 202, and which is rotated to urge the cellulosic feedstock through chamber 204 and sweep lower wall section 214.

In accordance with this particularly preferred aspect, paddles 228 and lower wall section 214 are configured such that when a given paddle is adjacent and passing over lower wall section 214, a substantially constant distance is maintained between the outer edge 236 of the paddle 228, and lower wall section 214. Such embodiments may aid in ensuring that the cellulosic material is urged forwardly at a substantially constant rate, and that the cellulosic material is not retained in the chamber.

Figure 5A:
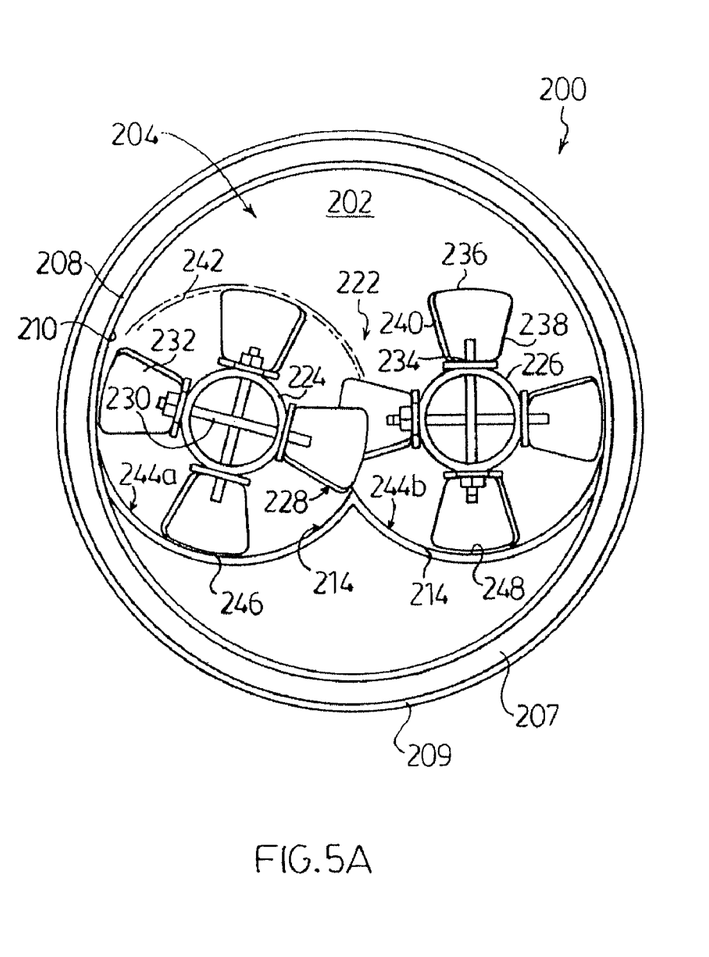
FIGS. 5A and 5B are transverse cross-sections taken along line 5-5 in FIG. 2, showing various rotational positions of an embodiment of a conveyance member of the present invention.

For example, in the embodiments shown, the outer edge 236 of each paddle is curved or arcuate in shape (see for example FIG. 7B), and the curve preferably matches an arc 242 swept or defined by the outer edge 236 as the shafts rotate (see for example FIG. 5A). Accordingly, when shafts 224 and 226 rotate, the outer edge 236 of each paddle 228 will describe a circle. That is, outer edge 236 of each blade 232 is curved to define a sector of a circle having a radius R1. It will be appreciated that in embodiments wherein the blades 232 are canted, the arc 242 swept by outer edge 236 will be 3-dimensional (i.e. will have a depth). When shafts 224 and 226 rotate, the outer edge 236 of each blade 232 will describe a circle having a radius R2 define R2 on the drawings. In embodiments wherein blades 232 are not canted, R2 will equal R1. In embodiments wherein blades 232 are canted, R2 will be less than R1.

Figure 5B:
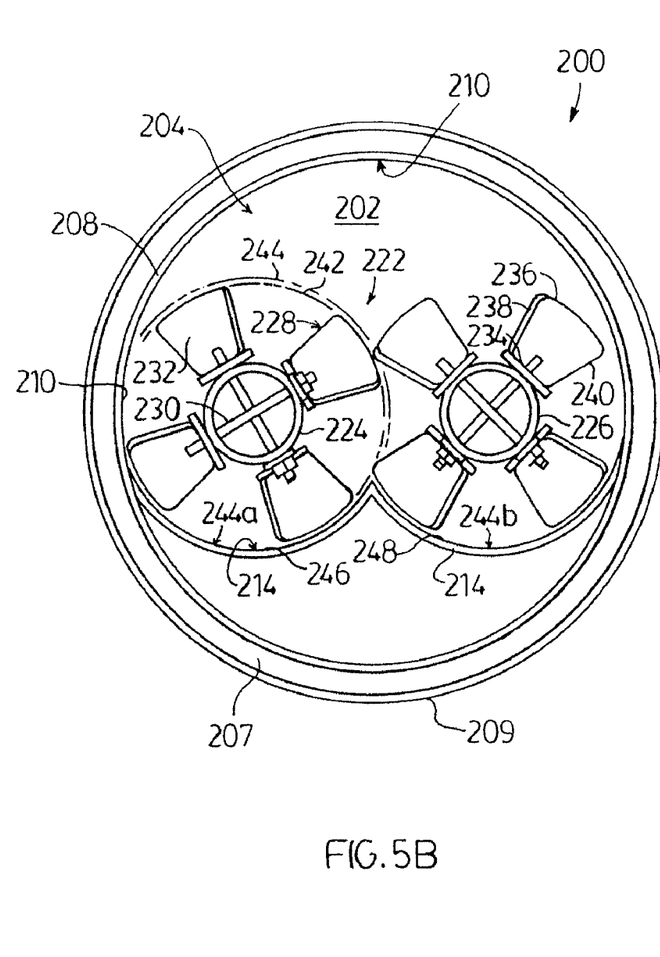
Figure 6:
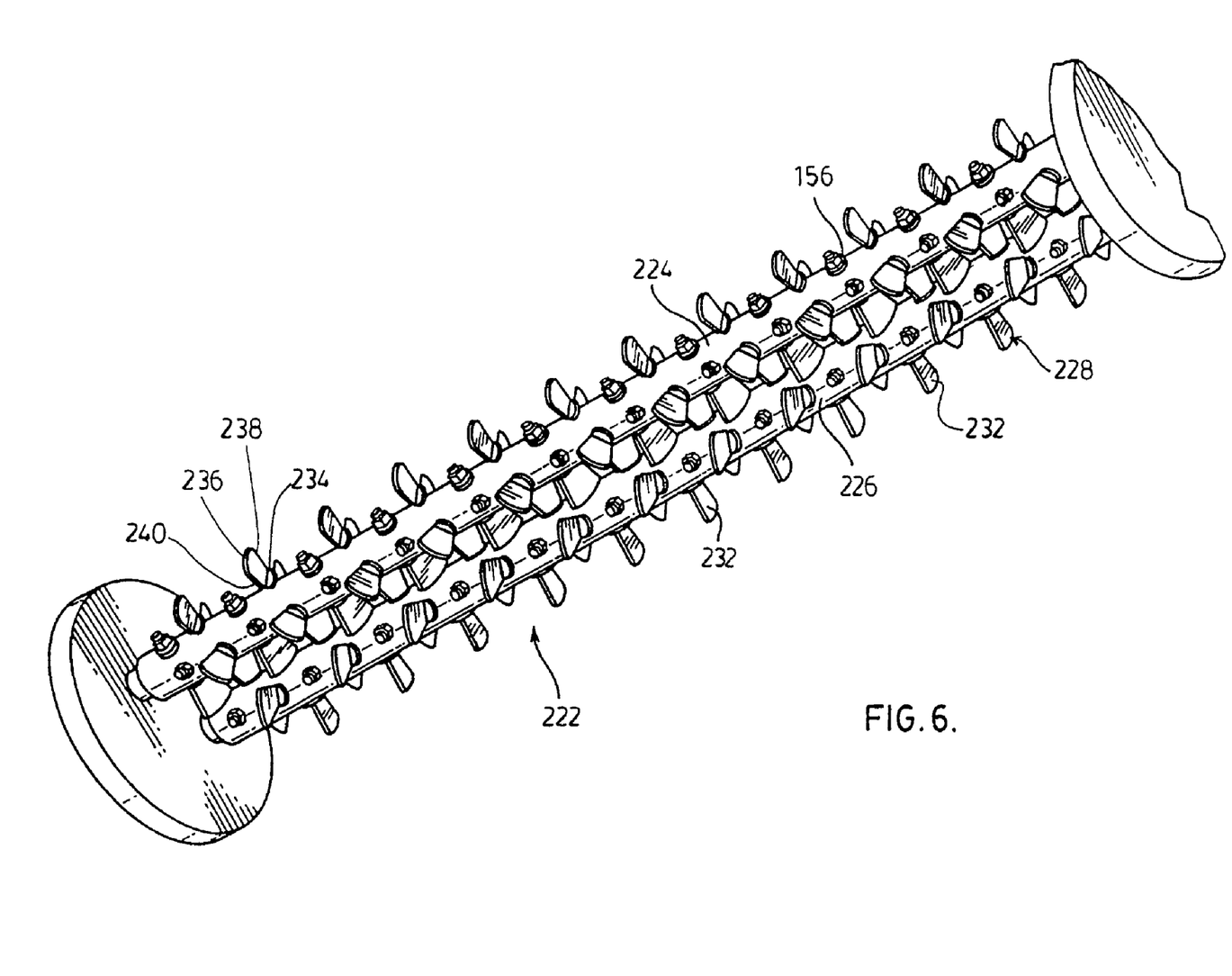
FIG. 6 is a perspective illustration of the conveyance member of FIG. 4.
Figures 7A, 7B, 7C, 7D:
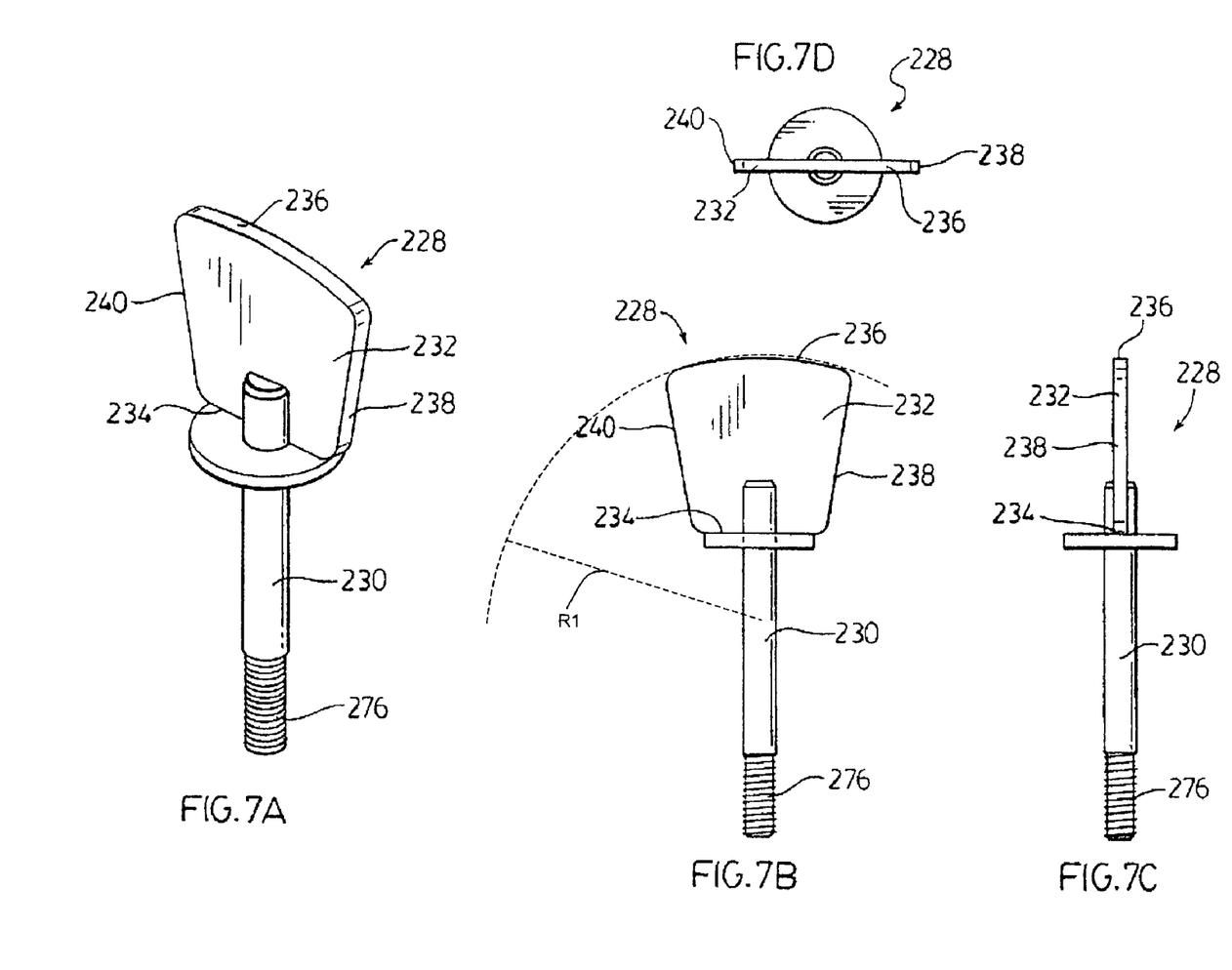
FIG. 7A is a perspective illustration of an embodiment of a paddle of the present invention.
FIG. 7B is a front plan view of the paddle of FIG. 7A.
FIG. 7C is a side plan view of the paddle of FIG. 7A.
FIG. 7D is a top plan view of the paddle of FIG. 7B.
Figures 8A, 8B, 8C, 8D:
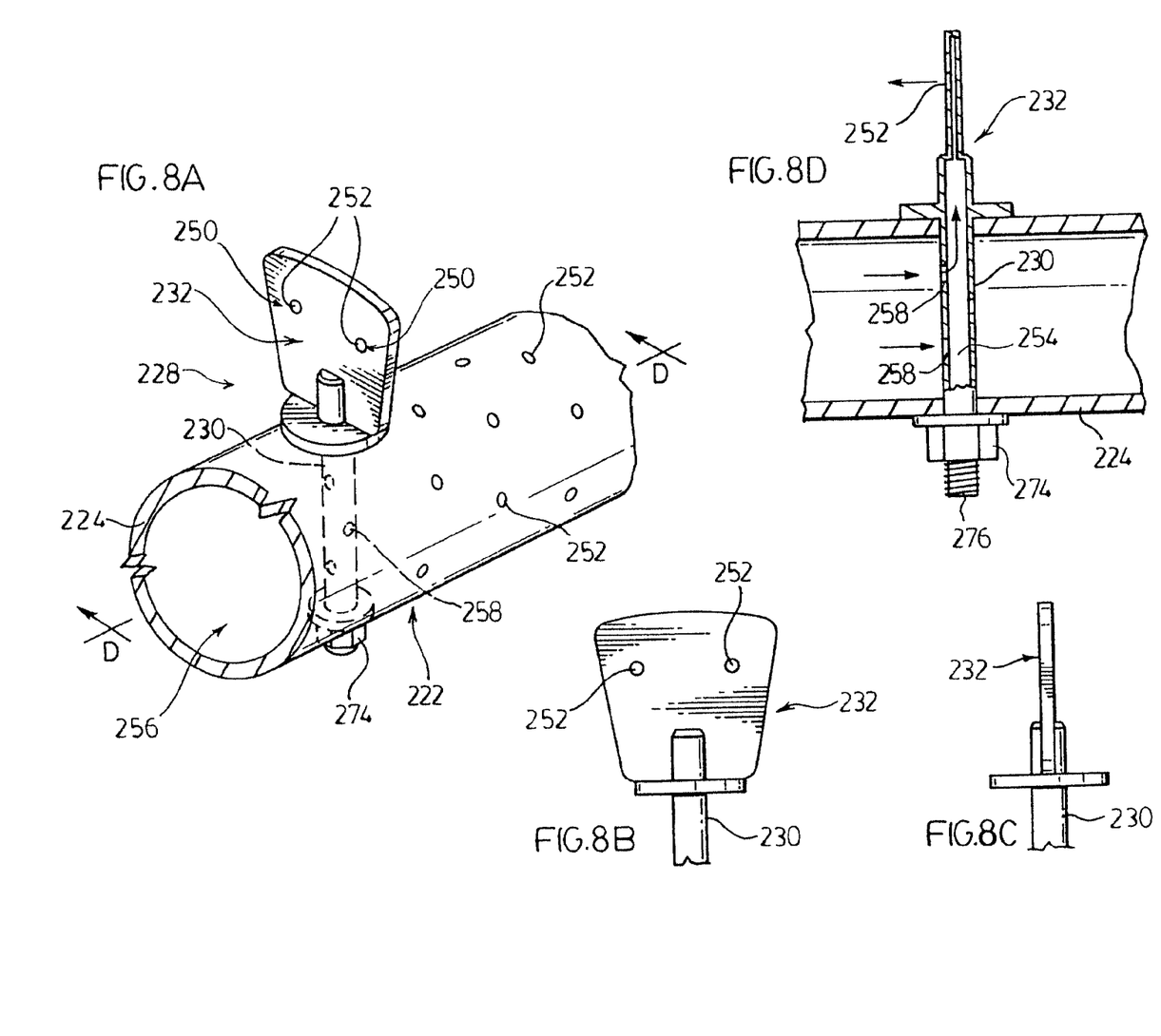
FIG. 8A is a partial perspective illustration of an embodiment of a conveyance member of the present invention, wherein the paddle of the conveyance member comprises injection ports.
FIG. 8B is a partial front plan view of the paddle of FIG. 8A.
FIG. 8C is a partial side plan view of the paddle of FIG. 8A.
FIG. 8D is a transverse cross-section taken along line D-D in FIG. 8A.

Further, in a preferred aspect, lower wall section 214 is configured such that in transverse section, as shown in FIGS. 5A-5B, lower wall section 214 defines at least one arc 244 and more preferably two or more arcs. In the embodiment shown, wherein conveyance member comprises two rotary shafts, lower wall section 214 defines two arcs 244a, 244b. That is, when viewed in transverse section, lower wall section 214 is scalloped. In alternate embodiments, wherein conveyance member comprises a different number of shafts, lower portion may define a different number of arcs, preferably one per shaft. Preferably, each shaft is centered above an arc 244.

Arcs 244a and 244b have a radius R3. Arc 244a comprises first portion 246 of lower wall section 214, and arc 244b comprises second portion 248 of lower wall section 214. First portion 246 is below first shaft 224, and second portion is below second shaft 226. Blades 232 and portions 246 and 248 are configured such that R3 is of a slightly greater radius than R2, for example less than about 6.5 mm greater than R2. Accordingly, when shafts 224 and 226 rotate, the paddles associated with shaft 224 will sweep along first portion 246, and the paddles associated with shaft 226 will sweep along second portion 248, such that a distance preferably less than about 6.5 mm is maintained between outer edge 236 of paddles 228 and first 246 and second 248 portions of lower wall section 214 as the paddles pass adjacent to lower wall section 214. The spacing between radial outer edge 236 and arc 244 may be from 2 to 15 mm. The spacing may vary depending upon the size of the particulate matter in the feedstock. The larger the size of the particulate matter, the larger the spacing may be. Preferably, the spacing is less than the maximum particle size and, more preferably, less than the median particle size. Accordingly, as the shafts rotate, particulate matter will be continually moved through the chamber. Further, if wall section 214 is heated, then the particulate matter will be inhibited from staying in the same location and being possibly overheated such that cellulose or hemicellulose is degraded by heat.

It will be appreciated that shafts 224, 226 may rotate in the same direction, or in opposite directions. Further, it will be appreciated that the rotation of shafts 224, 226 may be driven by a motor as exemplified, or another suitable means.

In accordance with a preferred embodiment, moisture is added to the cellulosic feedstock as the feedstock travels through the enclosed volume. Preferably, this step comprises adding moisture to increase the moisture content of the cellulosic feedstock from between about 5% and about 15 wt % to between about 30 to 60 wt %, preferably to between 45% and 55 wt %. The moisture may be added as liquid water, and/or may alternately be added as steam. If liquid water is used, it is preferably heated, for example, the liquid water may be heated to between about 50 to 70° C., preferably about 60° C. to about 70° C., and more preferably about 65° C. to about 70° C. It is preferred not to use steam since steam may result in the overheating of the cellulose and hemicellulose, causing degradation thereof. However, if the particularly preferred design exemplified herein is used, then higher temperatures may be used with reduced risk of degradation of the feedstock.

Additionally, the water may comprise additionally components. For example, one or more catalysts, including but not limited to mineral and organic acids, bases such as sodium hydroxide, organic solvents such as ethanol, and oxidizing agents such as hydrogen peroxide, may be added with the water.

The moisture may be added upstream from the chamber and/or in the chamber. The moisture may be added in a variety of ways, and is preferably added simultaneously at multiple spaced apart injection points. For example, referring to FIGS. 8A-8D, the injection points 250 may comprise a plurality of injection ports 252, which are provided in conveyance member 222 and/or in the inner wall 208 of the shell 206. In the embodiment of FIGS. 8A-8D, injection ports 252 are defined in blades 232 of paddles 228.

Alternately, or in addition, injection ports 252 may be provided in stems 230 and/or in shafts 224, 226. For example, in some embodiments, injection ports 252 are provided along the entire length L of chamber 204. In other embodiments, moisture injection ports 252 are preferably provided only in an upstream portion of chamber 204, preferably in the upstream half of the length L of chamber 204 and, more preferably in the first or upstream third $L_{1/3}$ of the length L of chamber 204 (see FIG. 4). For example, as exemplified in FIG. 1, a plurality of injection ports may be provided in the upper portion of chamber 204. As shown therein, one or more conduits 284 may convey water to a plurality of branch conduits 286 extending to different locations on the upper portion of chamber 204. The end of these conduits are in fluid flow communication with the interior of chamber 204, via a moisture addition member such as a nozzle or an open ended pipe or the like. As exemplified, six ports are provided. However additional or fewer ports may be used. Accordingly, moisture injection ports may additionally or alternately be provided in shell 206 of chamber 204. That is, injection points 250 may extend through wall 208, which defines inner surface of chamber 204 and/or wall section 214.

As shown, injection ports 252 of blades 232 are in fluid communication with one or more paddle ducts 254 provided within paddles 228. The one or more paddle ducts 254 are in fluid communication with a fluid conduit 256, which may extend through shafts 224, 226, for example via ports 258 provided in stem 230. Fluid conduits 256 are in fluid communication with a moisture source (not shown), for example at the ends 225, 227, of shafts 224, 226. Accordingly, as the conveyance member rotates, moisture is introduced into volume 202 by passing from a moisture source into fluid conduit 256, through ports 258 in stem 230, through paddle ducts 254, and out of ports 252.

In the above embodiments, the injection points may be positioned in a variety of configurations. In some embodiments, the injection points may be provided such that moisture is introduced into the cellulosic feedstock during its entire travel through chamber 204. For example, injection ports may be provided in shell 206 and/or in conveyance member 222 along the entire length of chamber 204. Preferably, the injection points may be provided such that moisture is introduced into the cellulosic feedstock during its initial travel through chamber 204. For example, the injection points may be provided only in a first portion, for example a first half and, more preferably, the first third, of the axial length of the impregnation chamber.

Furthermore, the number of injection points may vary depending on the particular embodiment. In some embodiments, wherein the injection points are provided in blades 232, each blade preferably comprises at least one injection port. In other embodiments, only some blades may comprise injection ports. Furthermore, in some embodiments, each blade comprises two injection ports; however in alternate embodiments, each blade may comprise one injection port, or greater than two injection ports. In some particular embodiments, chamber 204 is provided with a total of between 1 and 10 injection points.

In the preferred embodiment, the method optionally further comprises monitoring the moisture content of the feedstock as it passes through the volume. Accordingly, the amount of moisture introduced may be controlled in order to produce a feedstock having a predetermined moisture content. For example, one or more moisture sensors (not shown) may be positioned within chamber 204, for example upstream from inlet 211. As the feedstock passes through the chamber, the moisture sensors may measure the moisture content at various positions along the length of the chamber. When the moisture content of the feedstock reaches a predetermined value, for example between about 45% and about 55%, the addition of moisture to the chamber may be halted or reduced. In a further preferred embodiment, a controller (not shown) is operatively coupled to the moisture sensor(s) and controls the amount of moisture introduced based on the moisture content measured by the moisture sensor.

Alternately, and preferably in addition, the method also comprises heating the cellulosic feedstock as it travels through the volume. In some embodiments, the cellulosic feedstock is heated such that, when the feedstock exits the volume, the feedstock is at a temperature of between about 50 to about 65° C., preferably about 50° C. to about 70° C. when it exits outlet 213. Preferably, the cellulosic feedstock is provided to inlet 211 at less than about 30° C., and is heated to at least about 65° C. as it travels through the volume.

The cellulosic feedstock may be heated in a variety of ways. In some embodiments, the cellulosic feedstock may be heated directly. For example, as previously mentioned, in some embodiments, the moisture may be added as heated water. In such embodiments, in addition to providing moisture to the cellulosic feedstock, the heated water may serve to heat the cellulosic feedstock. Accordingly, in such embodiments, the method may comprise heating the moisture prior to contacting the moisture with the feedstock.

Figure 4:
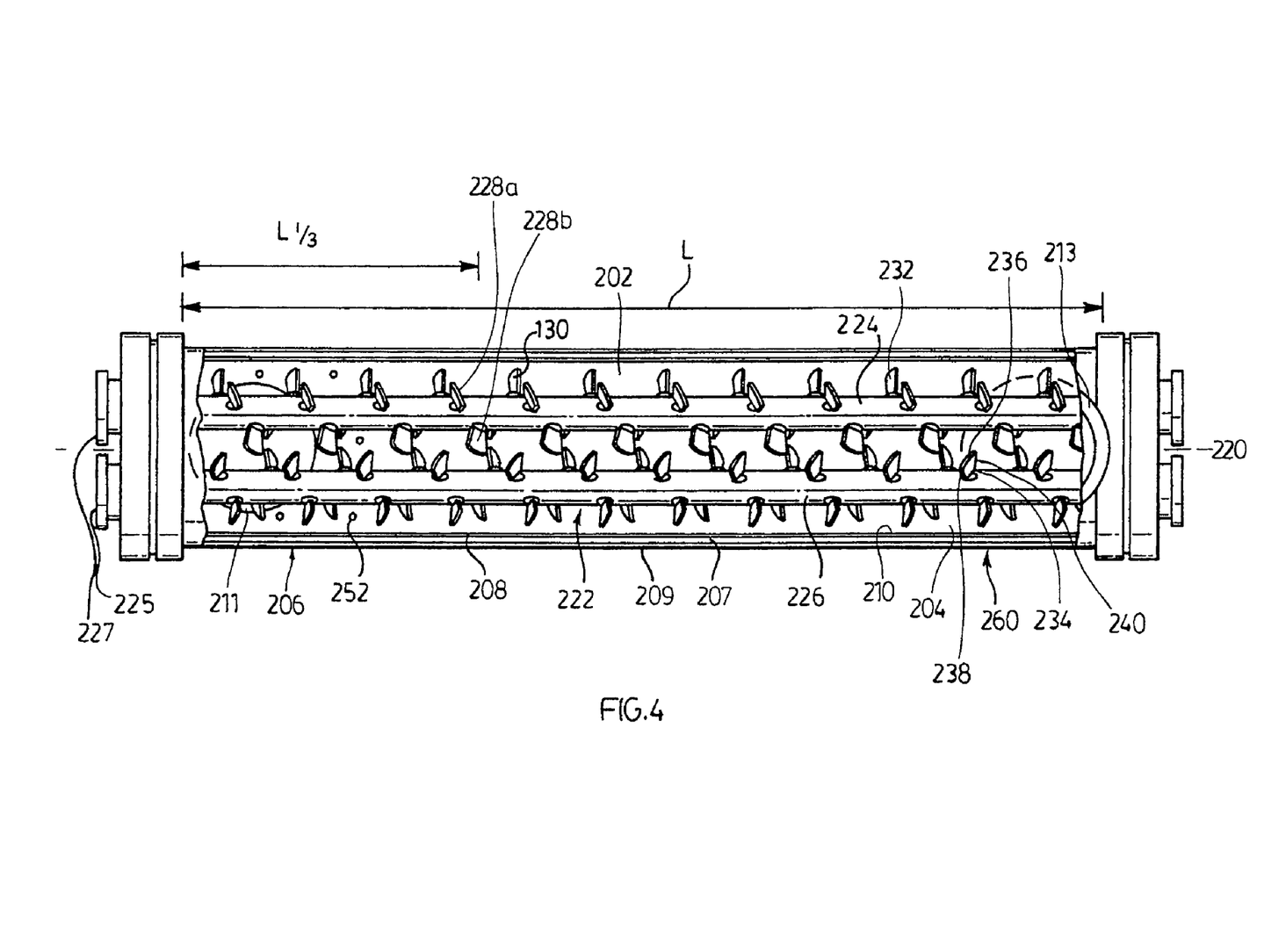
FIG. 4 is a cutaway top plan view of the mixing vessel of FIG. 1, wherein the upper portion of the shell has been removed showing a preferred embodiment of a conveyance member.

In other embodiments, the cellulosic feedstock may be heated indirectly. For example, the chamber walls 208 and/or the conveyance member may be heated. Referring to FIGS. 4 and 5, in the embodiments shown, the chamber walls 208 are heated by providing an outer wall 209, which surrounds at least a portion of shell 206. An enclosure 207 is defined between outer wall 209 and inner wall 208, and a heated fluid supply is associated with the enclosure. Enclosure 207 is in fluid communication at one end with one or more inlets, to which a heated fluid is supplied, and at the other end with one or more outlets, to which spent heated fluid is directed. Accordingly, the heated fluid circulates within enclosure 207, and provides heat to the cellulosic feedstock. The heated fluid may be water, for example, or steam. Any heating jacket or the like known in the art may be used.

The conveyance member preferably rotates at from 40 to 150 rpm and, more preferably, 45 to 75 rpm. Alternately, or in addition, the chamber may operate at a low fill factor, for example from 10 to 50 and preferably about 30%. Accordingly, a majority of the volume in chamber 204 may be filled with air. For example, if the fill factor is about 15-30%, then only 30% of the volume of chamber 204 is filled with feedstock, the rest being filled with, preferably air. As the conveyance member rotates, preferably at a relatively high speed, the feedstock will be thrown up into the empty upper portion of chamber 204 thereby mixing the feedstock to provide a more uniform distribution of heat and/or moisture throughout the feedstock. It will be appreciated that the use of a high rotational speed, combined with a low fill factor permits the use of a higher temperature in the heating jacket and/or in the temperature of the moisture provided to the feedstock in the chamber with reduced risk of heat degradation of the feedstock.

Accordingly, in one aspect, heat and/or moisture may be added in a chamber 204 and/or upstream thereof, wherein the conveyance member and the floor of the chamber are configured to permit the conveyance member to sweep the floor.

In another aspect, a chamber is utilized with a low fill volume and preferably a high rotational rate of the conveyance member to permit a higher heating temperature to be used with reduced risk of degradation of the cellulose and hemicellulose in the feedstock.

The cellulosic feedstock is preferably then subjected to activation and hydrolysis. The activation is preferably conducted by autohydrolysis. Autohydrolysis may be carried out directly after the treated feedstock exits the chamber or after a number of intermediate steps. For example, from outlet, the cellulosic feedstock may be directed to a holding tank 221 where it is stored for a period of time at an elevated temperature to further enhance the uniformity of the moisture and heat distribution, prior to being passed to an autohydrolysis reactor.

Accordingly, embodiments of the present invention provide a method and apparatus for heating and moistening a cellulosic feedstock, such that the cellulose of the feedstock is substantially accessible to hydrolysis enzymes. Furthermore, embodiments of the present invention provide a method and apparatus for heating and moistening a cellulosic feedstock while requiring substantially small amounts of heat and water. Accordingly, the process is substantially cost effective and energy efficient.

It will be appreciated that certain features of the invention, which are, for clarity, described in the context of separate embodiments or separate aspects, may also be provided in combination in a single embodiment. Conversely, various features of the invention, which are, for brevity, described in the context of a single embodiment or aspect, may also be provided separately or in any suitable sub-combination.

Although the invention has been described in conjunction with specific embodiments thereof, if is evident that many alternatives, modifications and variations will be apparent to those skilled in the art. Accordingly, it is intended to embrace all such alternatives, modifications and variations that fall within the spirit and broad scope of the appended claims. In addition, citation or identification of any reference in this application shall not be construed as an admission that such reference is available as prior art to the present invention.

We claim:

1. A method for treating a cellulosic feedstock, the method comprising:
   a) subjecting the cellulosic feedstock to impregnation comprising:
      (i) conveying the cellulosic feedstock having a moisture content through an enclosed volume;
      (ii) adding moisture to the cellulosic feedstock simultaneously at multiple spaced-apart moisture injection points as the cellulosic feedstock travels through the volume to increase the moisture content of the cellulosic feedstock from 5-15 wt % to 45-55 wt %;
      (iii) heating the cellulosic feedstock as it travels through the volume to about 50-70° Celsius whereby a heated moistened feedstock that has a relatively uniform temperature and moisture profile is obtained;
   b) subsequently subjecting the heated moistened feedstock to a downstream hydrolysis process in a steam explosion reactor to obtain an activated feedstock; and,
   c) subjecting the activated feedstock to an enzymatic hydrolysis process.

2. The method of claim 1, wherein the volume comprises an impregnation chamber defined by chamber walls having an inner surface, and the impregnation chamber extends longitudinally along an axial length from an inlet to an outlet, and the cellulosic feedstock is urged through the chamber by a conveyance member.

3. The method of claim 2, wherein the plurality of injection points comprises a plurality of ports extending through the chamber wall commencing proximate the inlet and the method further comprising introducing moisture to the cellulosic feedstock at least during its initial travel through the impregnation chamber.

4. The method of claim 3, wherein the injection points are provided in a first third of the axial length of the impregnation chamber.

5. The method of claim 1, further comprising adding heated water as at least part of the moisture.

6. The method of claim 1, further comprising adding a catalyst with the moisture.

7. The method of claim 2, wherein step (iii) comprises heating the cellulosic feedstock from less than about 30° Celsius at the inlet, to at least about 65° Celsius at the outlet.

8. The method of claim 1, wherein step (iii) comprises heating the moisture prior to contacting the moisture with the feedstock.

9. The method of claim 2, wherein step (iii) comprises indirectly heating the cellulosic feedstock by heating at least one of the chamber walls and the conveyance member.

10. The method of claim 2, wherein the conveyance member extends longitudinally through the impregnation chamber and is configured to urge the cellulosic feedstock axially through the impregnation chamber as the conveyance member rotates.

11. The method of claim 2, wherein the conveyance member comprises a rotary shaft extending longitudinally through the impregnation chamber and a plurality of paddles extending radially outwardly from the shaft, and the method further comprises rotating the shaft to urge the cellulosic feedstock axially through the impregnation chamber.

12. The method of claim 10, wherein the conveyance member includes moisture injection points and the method further comprises introducing moisture to the volume as the conveyance member rotates.

13. The method of claim 11, wherein the conveyance member includes a fluid conduit extending longitudinally through the shaft and a plurality of paddle ducts in communication with the fluid conduit and extending through the paddle to an outer surface thereof, and wherein the step of adding moisture to the cellulosic feedstock comprises injecting moisture into the feedstock through the paddle ducts.

14. The method of claim 2, wherein the conveyance member comprises a rotary shaft extending longitudinally through the impregnation chamber and a plurality of paddles extending radially outwardly from the shaft and the paddles are relative to the impregnation chamber to sweep at least a lower circumferential portion of the inner surface of the chamber walls when the feedstock is conveyed through the chamber.

15. The method of claim 2, wherein the conveyance member comprises a rotary shaft extending longitudinally through the impregnation chamber and a plurality of paddles extending radially outwardly from the shaft and the paddles are spaced and configured such that the lower circumferential portion of the chamber is swept along generally the entire axial length of the chamber as the feedstock is conveyed through the chamber.

16. The method of claim 1, wherein the feedstock in the volume has a residence time of less than about ten minutes.

17. The method of claim 1, further comprising monitoring the moisture content of the feedstock and introducing an amount of moisture to produce a moisture content of the heated moistened feedstock of 45-55 wt %.

18. The method of claim 1, further comprising providing a feedstock comprising fibers that have a length in the range of about 4 mm to about 7 mm.

19. The method of claim 1, further comprising prior to step (b), directing the heated moistened feedstock to a holding tank and removing the heated moistened feedstock from the holding tank and then subjecting the feedstock to the downstream hydrolysis process whereby an activated feedstock is obtained.

* * * * *